United States Patent
Klopf

(10) Patent No.: US 8,978,669 B2
(45) Date of Patent: Mar. 17, 2015

(54) DENTAL FLOSS DISPENSER WITH CLIP

(71) Applicant: Wanda S. Klopf, Naples, FL (US)

(72) Inventor: Wanda S. Klopf, Naples, FL (US)

( * ) Notice: Subject to any disclaimer, the term of this patent is extended or adjusted under 35 U.S.C. 154(b) by 0 days.

(21) Appl. No.: 14/251,721

(22) Filed: Apr. 14, 2014

(65) Prior Publication Data

US 2014/0251370 A1 Sep. 11, 2014

(51) Int. Cl.
*A61C 15/04* (2006.01)

(52) U.S. Cl.
CPC .................................... *A61C 15/043* (2013.01)
USPC ........................................................ 132/321

(58) Field of Classification Search
CPC .............................. A61C 15/04; A61C 15/043
USPC ................... 132/321, 324, 325, 329; D28/66; 222/99, 95; 24/3.12, 545–547, 555, 24/563, 570
See application file for complete search history.

(56) References Cited

U.S. PATENT DOCUMENTS

| | | | |
|---|---|---|---|
| 1,439,076 A * | 12/1922 | Edwards | 132/314 |
| 1,487,215 A * | 3/1924 | Dial | 132/325 |
| 4,788,082 A | 11/1988 | Schmitt | |
| 5,076,302 A | 12/1991 | Chari | |
| 5,332,107 A | 7/1994 | Williams | |
| 5,442,839 A * | 8/1995 | Miller | 24/563 |
| 5,449,092 A | 9/1995 | Bazan | |
| 5,732,722 A | 3/1998 | Mortvedt | |
| 6,572,063 B1 | 6/2003 | Gitelman et al. | |
| 6,749,088 B1 * | 6/2004 | Holevas | 222/99 |
| 7,198,051 B1 | 4/2007 | Festa | |
| 8,381,743 B1 | 2/2013 | Thomas et al. | |
| D686,019 S | 7/2013 | Lucsko | |
| 8,616,411 B1 * | 12/2013 | St. Germain | 222/99 |
| 2003/0140938 A1 | 7/2003 | Evans et al. | |

* cited by examiner

*Primary Examiner* — Rachel Steitz
(74) *Attorney, Agent, or Firm* — Livingston Loeffler, P.A.; Edward M. Livingston, Esq.; Bryan L. Loeffler, Esq.

(57) ABSTRACT

A dental floss dispenser (1) having a clip (2) located on a rear surface (11) of the dispenser for attaching the dispenser to a tube of toothpaste (5). The clip attaches to a lower edge of a tube of toothpaste and serves a dual purpose. The first purpose being to remind an individual to floss when brushing his or her teeth and the second purpose being to squeeze the toothpaste in the tube upward toward the opening of the tube as the toothpaste is dispensed out of the tube. The clip may also be a planar piece of material that is perpendicular to the dispenser and has a slot (18) that a lower edge of the tube is inserted into. The clip may be integrated into the dispenser or attached to the dispenser by a holder (10).

3 Claims, 3 Drawing Sheets

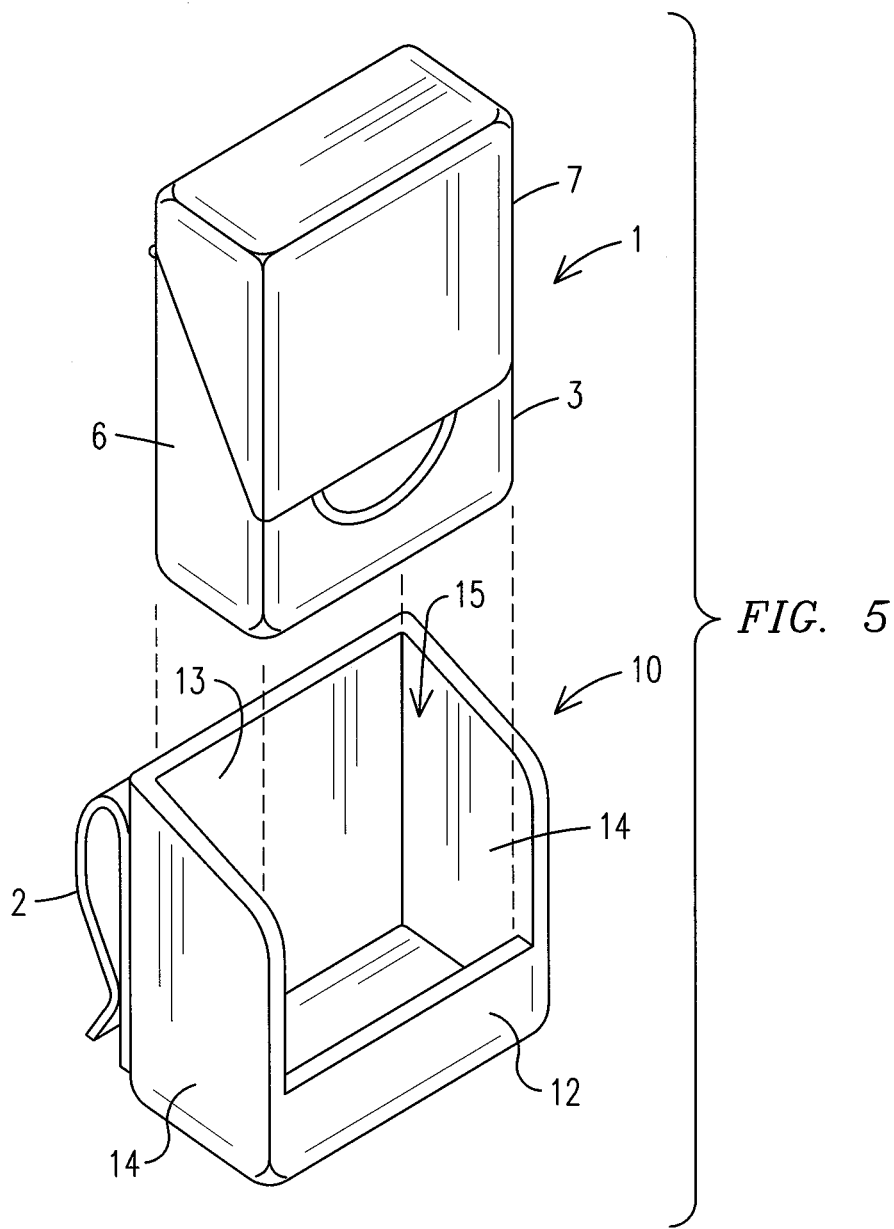
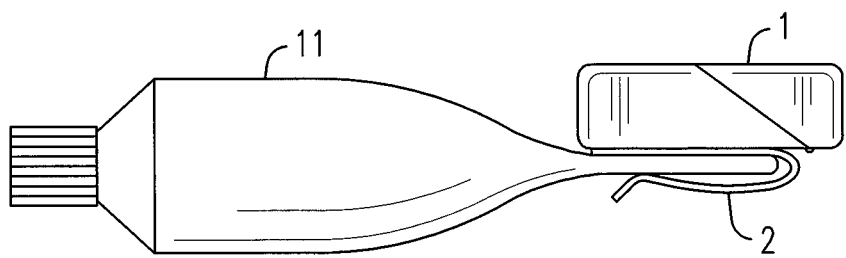
FIG. 5
FIG. 4

DENTAL FLOSS DISPENSER WITH CLIP

FIELD OF THE INVENTION

This invention relates to dental hygiene and, in particular, to a dental floss dispenser with a clip that allows the dental floss dispenser to be attached to a tube of toothpaste or to other articles.

BACKGROUND OF THE INVENTION

Dental floss is a bundle of thin filaments used to remove food and dental plaque from teeth. The floss is gently inserted between the teeth and scraped along the teeth sides.

Dental floss is commonly supplied in plastic dispensers that contain 10 to 100 meters of floss wrapped around a spool located within the dispenser. After pulling out the desired amount, the floss is pulled against a small protected blade in the dispenser to sever it.

Flossing in addition to tooth brushing can reduce plaque, gingivitis and halitosis compared to tooth brushing alone. The American Dental Association advises to floss thoroughly once or more per day. However, even with all of the benefits provided by flossing, many individuals forget to floss on a regular basis.

Therefore, a need exists for a device to keep dental floss readily available to individuals when brushing teeth so the individuals are reminded to floss.

The relevant prior art includes the following references:

| Pat. No. | Inventor | Issue/Publication Date |
| --- | --- | --- |
| (U.S. Patent References) | | |
| 4,788,082 | Vitelle | Oct. 18, 1988 |
| 5,076,302 | Chari | Dec. 31, 1991 |
| 5,332,107 | Williams | Jul. 26, 1994 |
| 5,449,092 | Bazan | Sep. 12, 1995 |
| 5,732,722 | Mortvedt | Mar. 31, 1998 |
| 6,572,063 | Gitelman et al. | Jun. 03, 2003 |
| 2003/0140938 | Evans et al. | Jul. 31, 2003 |
| 7,198,051 | Festa | Apr. 03, 2007 |
| 8,381,743 | Thomas et al. | Feb. 26, 2013 |
| D686,019 | Lucsko | Jul. 16, 2013 |
| (Foreign Patent References) | | |
| CN201261592 | N/A | Jun. 24, 2009 |
| CN102730256 | N/A | Oct. 17, 2012 |
| EP2422743 | Bosch Cerda | Aug. 14, 2013 |

SUMMARY OF THE INVENTION

The primary object of the present invention is to provide a clip for storing a dental floss dispenser on a tube of toothpaste to remind individuals to floss every time the toothpaste is used for brushing teeth.

An additional object of the present invention is to provide a clip for storing a dental floss dispenser on a tube of tooth paste that provides the convenience of keeping the dental floss together with the toothpaste.

An additional object of the present invention is to provide a clip for storing a dental floss dispenser on a tube of tooth paste that provides the benefit of squeezing the toothpaste toward the opening of the tube.

The present invention fulfills the above and other objects by providing a dental floss dispenser having a clip located on a rear surface of the dispenser for attaching the dispenser to a tube of toothpaste. The clip attaches to a lower edge of a tube of toothpaste and serves a dual purpose. The first purpose being to remind an individual to floss when brushing his or her teeth and the second purpose being to squeeze the toothpaste in the tube upward toward the opening of the tube as the toothpaste is dispensed out of the tube. The clip may also be a planar piece of material that is perpendicular to the dispenser and has a slot that a lower edge of the tube is inserted into. The clip may be integrated into the dispenser or attached to the dispenser by a holder that attaches to a conventional dental floss dispenser.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which:

FIG. 4 is a side view of a dental floss dispenser and clip of the present invention clipped to a tube of toothpaste;

FIG. 5 is an exploded front perspective view of a dental floss dispenser and holder with a clip of the present invention;

DESCRIPTION OF THE PREFERRED EMBODIMENTS

Figure 1:
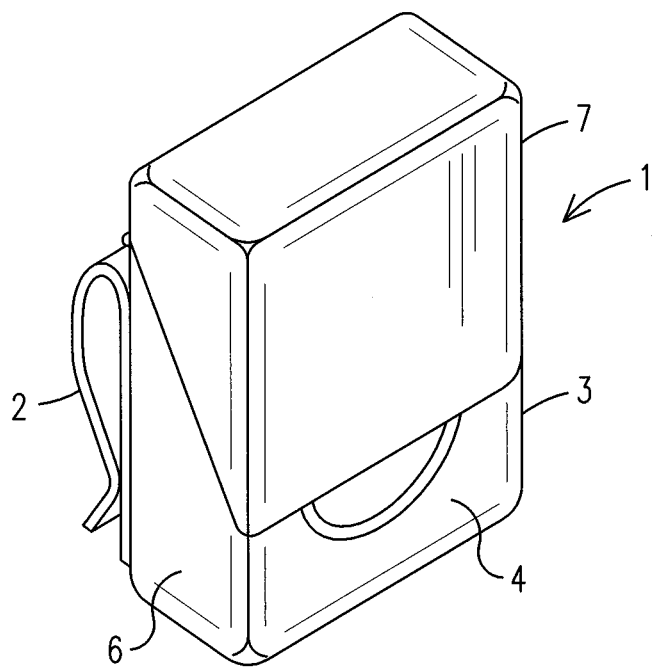
FIG. 1 is a front perspective view of a dental floss dispenser and clip of the present invention.
Figure 2:
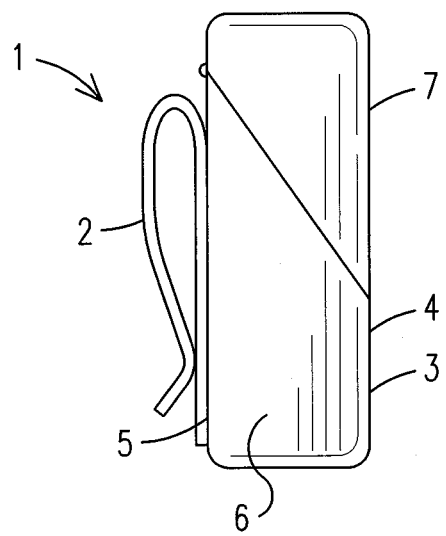
FIG. 2 is a side view of a dental floss dispenser and clip of the present invention.
Figure 3:
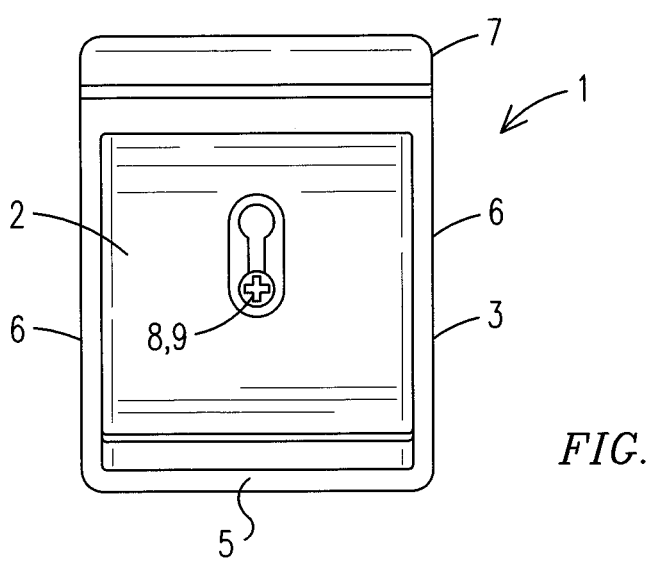
FIG. 3 is a rear view of a dental floss dispenser and clip of the present invention.
Figure 6:
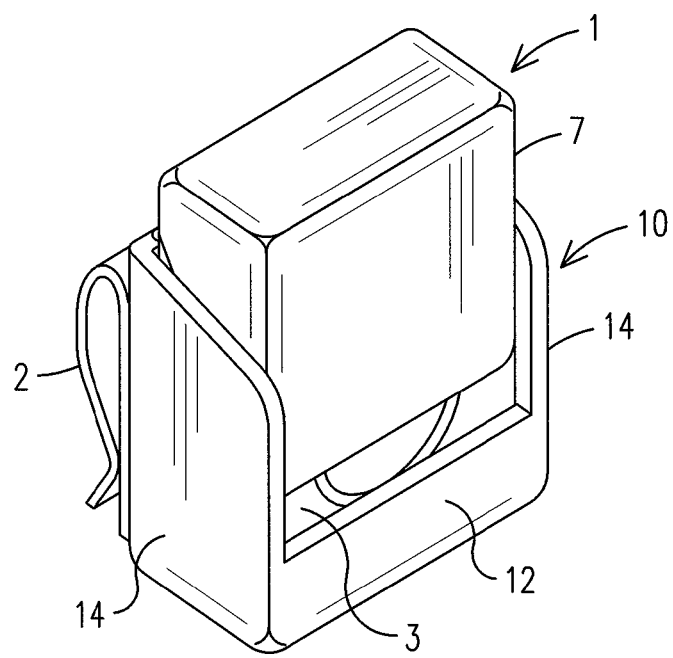
FIG. 6 is a front perspective view of a dental floss dispenser and holder with a clip of the present invention.

For purposes of describing the preferred embodiment, the terminology used in reference to the numbered components in the drawings is as follows:

1. dental floss dispenser
2. clip
3. housing of dental floss dispenser
4. front surface of dental floss dispenser
5. rear surface of dental floss dispenser
6. side surface of dental floss dispenser
7. lid of dental floss dispenser
8. attachment means
9. screw
10. holder
11. tube of toothpaste
12. front panel of holder
13. rear panel of holder
14. side panel of holder
15. opening of holder
16. slotted clip
17. slot With reference to FIGS. 1, 2 and 3, a front perspective view, a side view, and a rear view, respectively, of a dental floss dispenser 1 and clip 2 of the present invention are illustrated. The dental floss dispenser 1 comprises a housing 3 having a front surface 4, rear surface 5, and side surfaces 6. Dental floss is stored within the housing 3 and access by opening a lid 7 hingedly attached to the housing 3. The clip 2 is attached to the housing 3 (preferably on the rear surface 5) via an attachment means 8, such a screw 9, rivet, adhesive, welding, pressure fitting, male/female connection, a holder 10 (as illustrated in FIGS. 5-6) and so forth. When using a screw 9 or other attachment means 8 that may project into the housing 3, the screw is preferable centered over a center of a spool located within the housing 3 so the screw 9 will not interfere with the rotation of the spool when dental floss is being pulled out of the housing 3 for use. The clip 2 may also be integral to the dental floss dispenser 1.

With reference to FIG. 4, a side view of a dental floss dispenser 1 and clip 2 of the present invention clipped to a tube of toothpaste 11, is illustrated. The clip 2 is preferably substantially U-shaped so it can be slid over the end of a tube of toothpaste 11 to squeeze the toothpaste in the tube 11 upward toward the opening of the tube 11 as the toothpaste is dispensed out of the tube 11.

With reference to FIGS. 5 and 6, an exploded front perspective view and a front perspective view, respectively, of a dental floss dispenser 1 and holder 9 with a clip 2 of the present invention are illustrated. The holder 9 comprises at least one front panel 12, a rear panel 13 and side panels 14 creating an opening 15 into which the dental floss dispenser 2 is inserted into the holder 9. The clip 2 is attached to the holder 9 (preferably on the rear panel 5) via an attachment means 8, such a screw, rivet, adhesive, welding, pressure fitting, male/female connection, stud, slot and so forth. The clip 2 may also be integral to the dental holder 9. The at least one front panel 12 of the holder 9 preferably has a height that is less than a height of the front surface 4 of the housing 3, thereby allowing the lid 7 to be opened without the any interference from the housing 3. Likewise, the rear panel 13 of the holder 9 preferably has a height that is less than a height of the rear surface 5 of the housing 3, thereby allowing the lid 7 to be opened without the any interference from the housing 3

Figure 7:
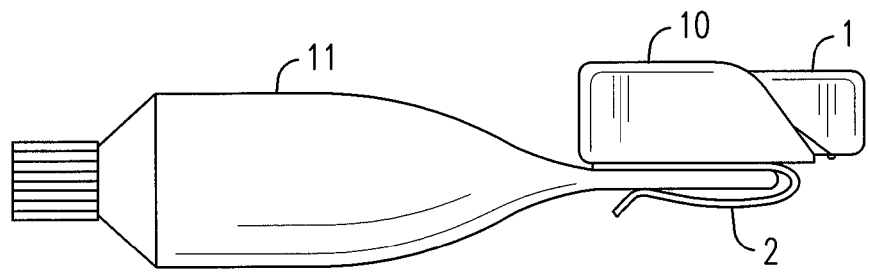
FIG. 7 is a side view of a dental floss dispenser and holder with a clip of the present invention clipped to a tube of toothpaste.

With reference to FIG. 7, a side view of a dental floss dispenser 1 and holder 9 with a clip 2 of the present invention clipped to a tube of toothpaste 11, is illustrated. The clip 2 is preferably substantially U-shaped so it can be slid over the end of a tube of toothpaste 11 to squeeze the toothpaste in the tube 11 upward toward the opening of the tube 11 as the toothpaste is dispensed out of the tube 11.

Figure 8:
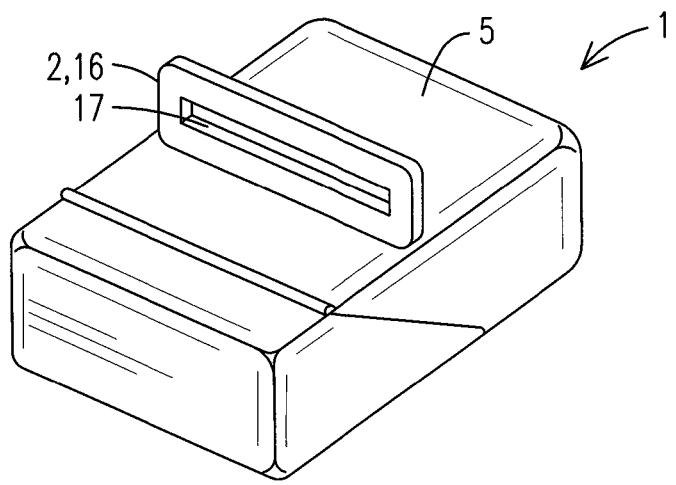
FIG. 8 is a dental floss dispenser having a slotted clip of the present invention.

Finally, with reference to FIG. 8, a dental floss dispenser 1 having a slotted clip 2, 16 of the present invention is illustrated. The slotted clip 2, 16 comprises a planar piece of material that is perpendicular to the rear surface 5 of the dental floss dispenser 2 and has a slot 17 that a lower edge of a tube of toothpaste 11 may be inserted into. The slotted clip 2, 16 is attached to the housing 3 (preferably on the rear surface 5) via an attachment means 8, such a screw 9, rivet, adhesive, welding, pressure fitting, male/female connection, a holder 10 (as illustrated in FIGS. 5-6) and so forth. The slotted clip 2, 16 may also be integral to the dental floss dispenser 1.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A dental floss dispenser comprising:
    an enclosed housing having a rectangular-shaped front surface, rectangular-shaped rear surface and rectangular-shaped side surfaces;
    dental floss stored on a spool within said enclosed housing and access to said dental floss provided by a lid that is hingedly attached to the enclosed housing;
    a clip extending from the rectangular-shaped rear surface of the enclosed housing;
    said clip having a closed end and being open on at least three sides so said clip can be slid over a tube of toothpaste and held in place on the tube of toothpaste via a pressure fit; and
    said clip being in a parallel position in relation to the rectangular-shaped rear surface of the enclosed housing.

2. A dental floss dispenser comprising:
    an enclosed housing having a rectangular-shaped front surface, rectangular-shaped rear surface and rectangular-shaped side surfaces, thereby creating a cuboidal-shaped enclosed housing;
    dental floss stored on a spool within said enclosed housing;
    access to said dental floss provided by a lid that is hingedly attached to the enclosed housing;
    a clip extending from the rectangular-shaped rear surface of the enclosed housing;
    said clip having a closed end and being open on at least three sides so said clip can be slid over a tube of toothpaste and held in place on the tube of toothpaste via a pressure fit; and
    said clip being in a parallel position in relation to the rectangular-shaped rear surface of the enclosed housing.

3. A dental floss dispenser comprising:
    an enclosed housing having a planar front surface, a planar rear surface and at least one side surface;
    dental floss stored within said enclosed housing;
    a clip extending from the planar rear surface of the enclosed housing;
    said clip having a closed end and being open on at least three sides so said clip can be slid over a tube of toothpaste and held in place on the tube of toothpaste via a pressure fit; and
    said clip being in a parallel position in relation to the planar rear surface of the enclosed housing.

* * * * *